United States Patent [19]

Siever

[11] Patent Number: 5,709,645
[45] Date of Patent: Jan. 20, 1998

[54] INDEPENDENT FIELD PHOTIC STIMULATOR

[75] Inventor: David Siever, Edmonton, Canada

[73] Assignee: Comptronic Devices Limited, Edmonton, Canada

[21] Appl. No.: 593,871

[22] Filed: Jan. 30, 1996

[51] Int. Cl.$^6$ ............................................. A61N 5/06
[52] U.S. Cl. ............................... 600/27; 600/26; 607/88
[58] Field of Search .......................... 128/731, 732, 128/745; 600/26, 27; 607/88-91

[56] References Cited

U.S. PATENT DOCUMENTS

| | | | |
|---|---|---|---|
| 3,576,185 | 4/1971 | Schulz et al. | |
| 3,612,651 | 10/1971 | McCurdy | 350/145 |
| 3,712,292 | 1/1973 | Zentmeyer, Jr. | |
| 3,773,049 | 11/1973 | Rabichev et al. | |
| 3,826,250 | 7/1974 | Adams | |
| 3,857,383 | 12/1974 | Sommerfeld et al. | |
| 4,315,502 | 2/1982 | Gorges | 128/1 C |
| 5,306,228 | 4/1994 | Rubins | 600/27 |
| 5,562,719 | 10/1996 | Lopez-Claros | 607/88 |

*Primary Examiner*—Jennifer Bahr
*Assistant Examiner*—Rosiland Kearney

[57] ABSTRACT

A photic stimulator for stimulating the central nervous system and the brain waves of a human subject having left and right eyes and left and right visual fields within each eye. The stimulator includes light assemblies providing pulsating light signals individually to the left and right visual fields of each of the left and right eyes of the subject and a control module for varying frequency and intensity of the light assemblies. The photic stimulator can stimulate the left and right visual fields of each eye independently of each other. This capability exploits the anatomical structure of the optic chiasm found within the human brain where stimuli of both eyes stimulates the side of the visual cortex opposite the side where the visual stimulation is seen in the visual field.

19 Claims, 2 Drawing Sheets

INDEPENDENT FIELD PHOTIC STIMULATOR

FIELD THE INVENTION

This invention relates to the field of systems for stimulating the central nervous system and more particularly to a device for releasing psychological and physiological stress and tension, and for the treatment of certain medical conditions by stimulating the senses of sight.

BACKGROUND OF THE INVENTION

It is widely supported in the field of psychology and learning that the left hemisphere of the brain is the source of logical reasoning and rote functioning of the human consciousness. Conversely, the right brain hemisphere is the source of artistic, creative and imaginative functioning within the brain.

Various prior art systems have been developed for use in stimulating and patterning these brain functions. For example, U.S. Pat. No. 4,315,502 issued Feb. 16, 1982 teaches an apparatus for stimulating and coordinating whole brain wave function. The apparatus includes a combination of a source of pulsating light in an eye-covering mask that locates the light sources adjacent the left and right eyes of a subject and an audio headset that applies sound signals to the ears of the subject.

The problem with these whole eye stimulation systems is that they do not account for the distinct visual fields that exist in each eye. It has been found that the left visual field of both eyes elicit responses from the right visual cortex of the brain; and the right visual field of both eyes elicit responses from the left visual cortex of the brain. This visual field concept permits better control over left and right brain stimulation.

Consequently, there is a need for a photic stimulator capable of stimulating the left and right visual fields of each eye independently of each other.

SUMMARY OF THE INVENTION

An object of the present invention is to provide a photic stimulator capable of stimulating the left and right visual fields of each eye independently of each other.

In accordance with one aspect of the present invention there is provided an apparatus for stimulating the central nervous system and the brain waves of a human subject having left and right eyes and left and right visual fields within each eye comprising: light means providing pulsating light signals individually to the left and right visual fields of each of the left and right eyes of the subject; and a control module for varying frequency and intensity of the light means.

In accordance with another aspect of the present invention there is provided a method of stimulating the central nervous system and the brain waves of a human subject having left and right eyes and left and right visual fields within each eye comprising: providing pulsating light signals individually to the left and right visual fields of each of the left and right eyes of the subject; and varying frequency and intensity of the light signals.

BRIEF DESCRIPTION OF THE DRAWINGS

Embodiments of the invention will be described by way of example in conjunction with the drawings in which.

DETAILED DESCRIPTION EMBODIMENTS OF THE INVENTION

Figure 1A:
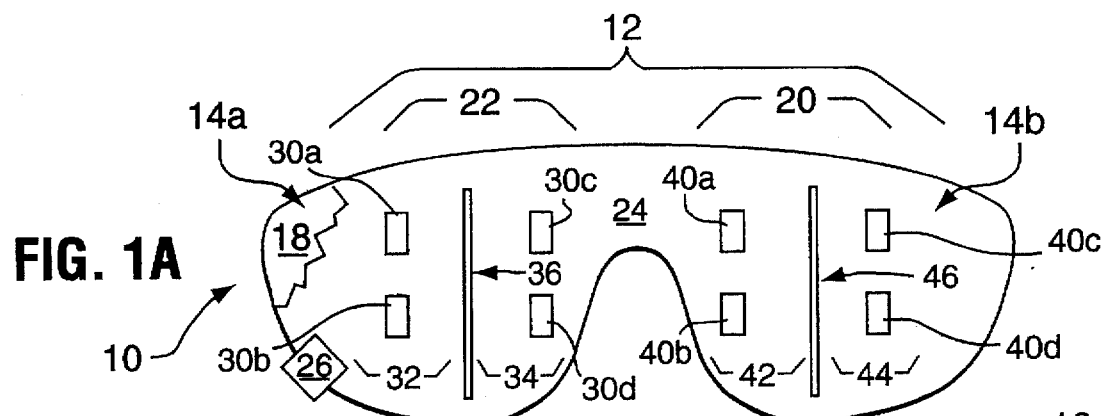
FIG. 1A illustrates a plan view of a photic stimulator according to an embodiment of the present invention.
Figure 1B:
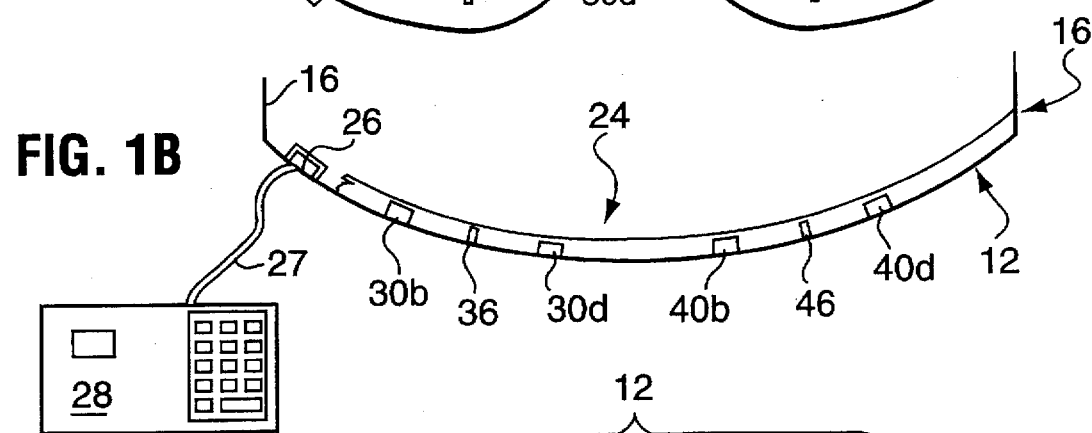
FIG. 1B illustrates a bottom view of the photic stimulator shown in FIG. 1A.

FIGS. 1A and 1B illustrate an embodiment of a photic stimulator 10 according the present invention. The photic stimulator 10 includes an eye mask 12 having eye pieces 14a, 14b that is worn covering the eyes of a human subject (not shown) and is held in place by a pair of hinged arms 16 adapted to rest on the ears of the subject.

The stimulator 10 includes a reflective layer 18 attached to the inside surface of the eye pieces 14a, 14b; right and left light-producing assemblies 20 and 22; a cover 24 placed over the light-producing assemblies 20 and 22; and a connector 26.

As shown in FIGS. 1A and 1B, the eye mask 12 is preferably a pair of glasses, but other forms of eye masks can be used such as goggles. The reflective layer 18 attached to the eye pieces 14a and 14b ensures that light generated from the light-producing assemblies 20 and 22 remains within the eye mask 12 and does not pass through the eye pieces 14a and 14b. The reflective layer 18 can be made from silver colored mylar, aluminum foil or silver painted materials.

The cover 24 is placed over the light-producing assemblies 20 and 22 to permit light transfer to the subject's eyes and to protect the assemblies 20 and 22 from contamination. The cover 24 can be made from clear glass, transparent or translucent color filters, prismatic lenses, opaque lenses or any combination of these forms. The choice of cover 24 is at least partially dependent on the type of light source used in the light-producing assemblies 20 and 22 as fully described hereinafter.

The connector 26 receives a cord 27 from a control module 28 to supply voltage and control signals to the light-producing assemblies 20 and 22.

The left light-producing assembly 22 includes four light sources 30a, 30b, 30c, and 30d that represent incandescent bulbs. The light sources 30a–d are mounted in vertical pairs (one pair defined by 30a, 30b and the other pair defined by 30c, 30d) thereby dividing the left light-producing assembly 22 into a left visual field 32 and a right visual field 34.

The light source pairs 30a,b and 30c,d are preferably spaced by approximately 1 inch (2.5 cm). The light source pairs 30a,c and 30b,d are preferably spaced by approximately 8/10ths of 1 inch (2 cm).

A left light blocker 36 is placed between the light source pairs 30a,b and 30c,d. The blocker 36 provides a vertical barrier to block the light emitted from one pair of light sources (for example, 30a,b) from reaching the other pair of light sources (for example, 30c,d) or from illuminating more than its associated half of the visual field (i.e. light sources 30a,b illuminates visual field 32 and light sources 30c,d illuminates visual field 34).

The right light-producing assembly 20 also includes four light sources 40a, 40b, 40c, and 40d that represent incandescent bulbs. The light sources 40a–d are mounted in vertical pairs (one pair defined by 40a, 40b and the other pair defined by 40c, 40d) thereby dividing the right light-producing assembly 20 into a left visual field 42 and a right visual field Spacing of light sources 40a–d relative to each other is identical to the spacing discussed above in conjunction with light sources 30a–d.

A right light blocker 46 is placed between the light source pairs 40a,b and 40c,d. The blocker 46 provides a vertical barrier to block the light emitted from the pairs of light sources as discussed above in conjunction with the left light blocker 36.

The light blockers 36 and 46 can be made from a black rubber or plastic material. Each of the blockers 36 and 46 is respectively aligned with the center of the pupil of the eye of an average person, thereby separating the visual fields (32/34 and 42/44) of the eyes of the subject when the mask 12 is worn. For certain subjects such as children or persons with eye abnormalities the blockers 36 and 46 can be biased slightly to the right or left as required.

Figure 2A:
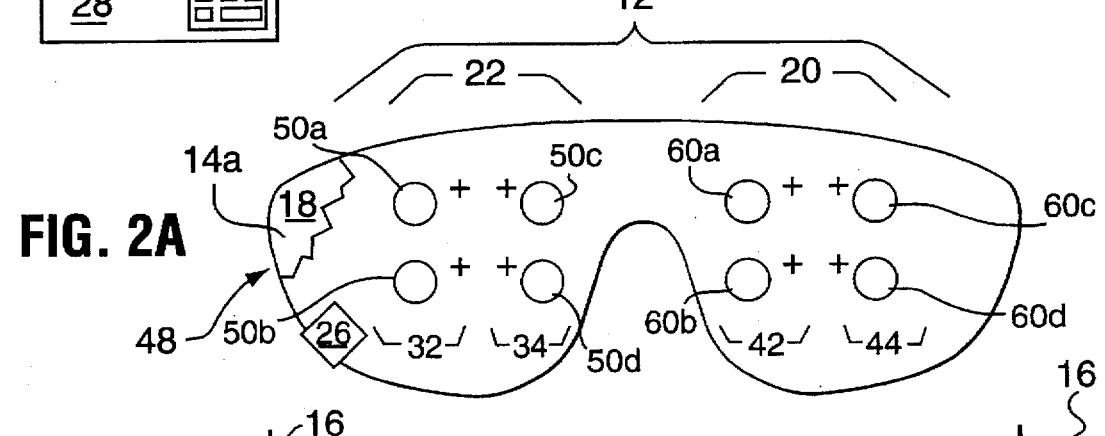
FIG. 2A illustrates a plan view of a photic stimulator according to another embodiment of the present invention.
Figure 2B:
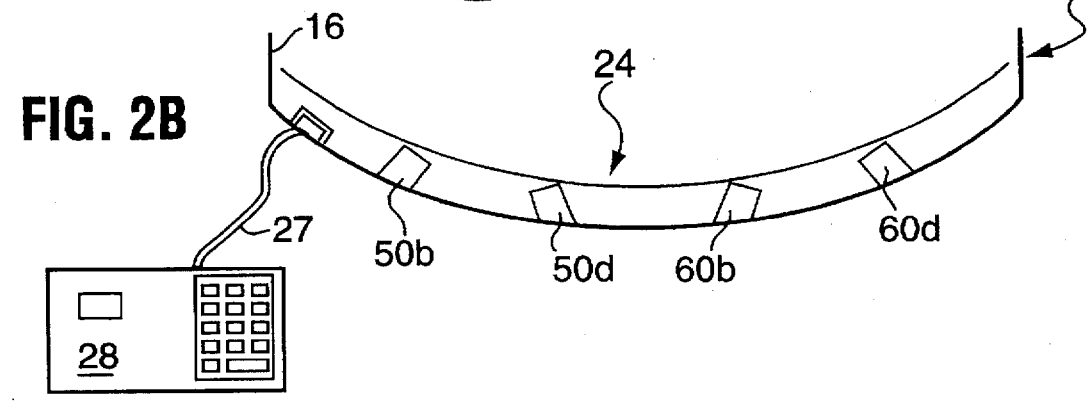
FIG. 2B illustrates a bottom view of the photic stimulator shown in FIG. 2A.

FIGS. 2A and 2B illustrate another embodiment of a photic stimulator 48 according the present invention. The photic stimulator 48 is similar to the stimulator 10 shown in FIGS. 1A and 1B. Like reference numerals in FIGS. 2A and 2B represent the same item discussed in conjunction with FIGS. 1A and 1B.

The stimulator 48 is distinguished from stimulator 10 by the use of light emitting diodes (LEDs) as light sources 50a, 50b, 50c, and 50d for the left assembly 22 and light sources 60a, 60b, 60c, and 60d for the right assembly 20. The LEDs are aimed in a direction such that the light source pairs 50a,b/60a,b and 50c,d/60c,d will illuminate approximately one-half half of the subject's visual field of a particular eye.

No vertical barrier (such as the light blockers 36 and 46 shown in FIGS. 1A and 1B) is required since the light produced by the LED pairs (50a,b/50c,d and 60a,b/60c,d) can be controlled not to interfere with each other.

Figure 3:
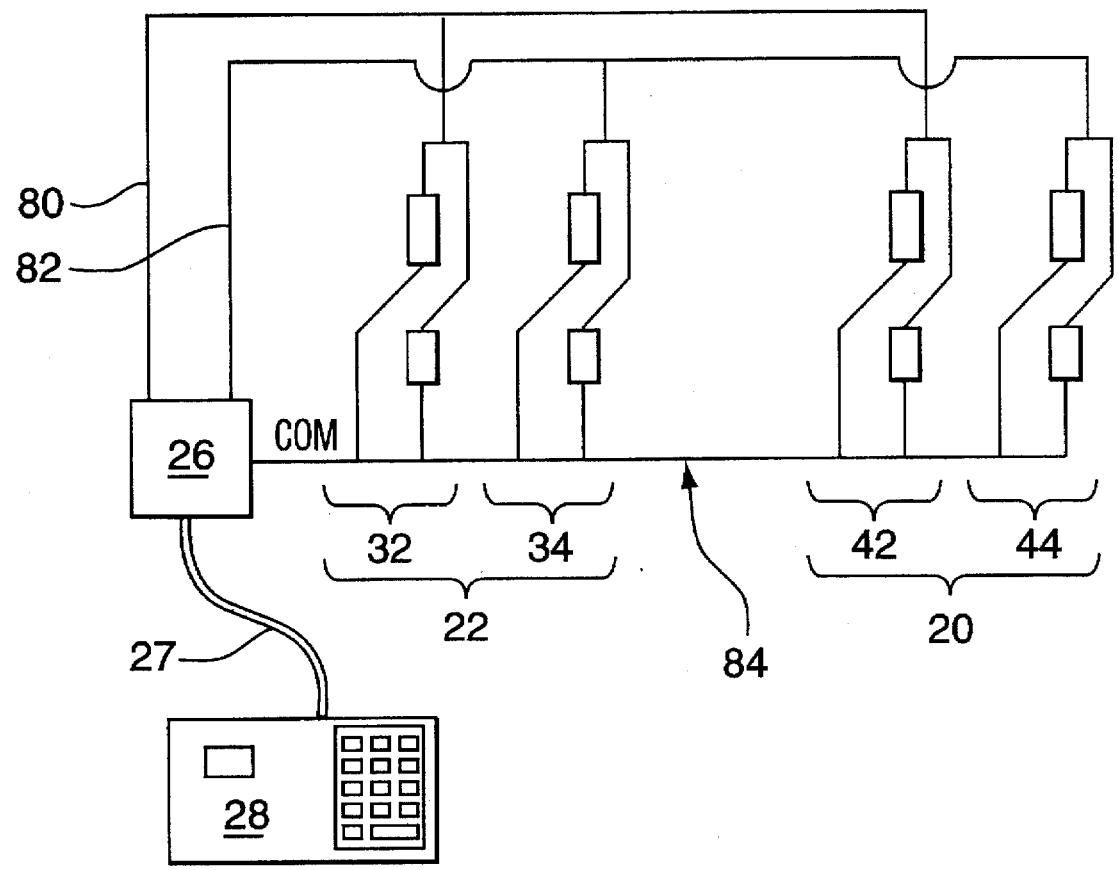
FIG. 3 illustrates a schematic diagram of the electrical connections of the photic stimulator shown in FIG. 1A and FIG. 2A.

FIG. 3 illustrates an electrical schematic of the light sources (30a–d, 40a–d, 50a–d, or 60a–d) interconnection pattern. The left visual fields 32 and 42 of the right and left light-producing assemblies 20 and 22 are electrically connected by a left bus line 80. The right fields 34 and 44 of the right and left light-producing assemblies 20 and 22 are electrically connected by a right bus line 82. The right and left bus lines 80 and 82 are both electrically attached to the connector 26. A common return bus line 84 connects the light-producing assemblies 20 and 22 to the connector 26.

When the LED light sources 50a–d are used a positive voltage is applied to the (+) lead of the LED and a negative voltage is applied to the (−) lead of the LED.

The cord 27 is a three conductor electrical cord that is attached to the connector 26 to provide the necessary control signals to the assemblies 20 and 22. The control module 28 provides the necessary power to the light producing assemblies 20 and 22. The power supplied by the module 28 can be oscillated to a variety of brain wave frequencies.

The module 28 controls power supplied to the left visual fields 32 and 42 of the right and left light producing assemblies 20 and 22 at a frequency different from and independent of the right visual fields 34 and 44 of the right and left light-producing assemblies 20 and 22. The module 28 can turn the light assemblies 20 and 22 on and off rapidly; sinusoidally or in other wave forms.

Various control modules 28 are known in the art to provide the described frequency control, such as the DAVID Paradise XL™, DAVID Paradise™, DAVID Paradise Jr.™ or the DAVID 2001™. All of these control modules are capable of providing a frequency of stimulation in which the left fields can be stimulated at a different frequency from the right fields. In addition, the DAVID Paradise XL includes software that enables subjects to custom design their own personal brain wave entrainment sessions via a standard personal computer.

The photic stimulators 10 and 48 of the present invention can stimulate the left and right visual fields 32/42 and 34/44 of each eye independently of each other. This capability exploits the anatomical structure of the optic chiasm found within the human brain where stimuli of both eyes stimulates the side of the visual cortex opposite the side where the visual stimulation is seen in the visual field.

For example, by flashing light sources 30a,b and 40a,b of stimulator 10 (i.e. the left visual fields 32 and 34 of both eyes) an evoked response is elicited within the right visual cortex of the brain. By flashing light sources 30c,d and 40c,d of stimulator 10 (i.e. the right visual fields 34 and 44 of both eyes) an evoked response is elicited within the left visual cortex of the brain. This stimulation control allows one visual cortex to be stimulated in alpha (i.e. sleep) while the other visual field can be awakened by being stimulated at higher frequencies.

EXAMPLES

The following examples illustrate various frequency therapies and the intended results on the subject:

(1) A frequency of approximately 8 to 12 Hz applied to the right visuals field 34/44 of both eyes and a frequency of approximately 12 to 16 Hz to the left visual field 32/42 of both eyes appears to be effective in treating attention deficient disorder (ADD) in children.

(2) A frequency of approximately 10 to 14 Hz applied to the right visuals field 34/44 of both eyes and a frequency of approximately 16 to 20 Hz to the left visual field 32/42 of both eyes appears to be effective in treating ADD in adolescent children.

EXAMPLES (Cont.)

(3) A frequency of approximately 12 to 16 Hz applied to the right visuals field 34/44 of both eyes and a frequency of approximately 21 to 26 Hz to the left visual field 32/42 of both eyes appears to be effective in treating ADD in adults.

(4) An alpha frequency (10 Hz) applied to the right visual fields 34/44 of both eyes and a 25 Hz frequency applied to the left visual fields 32/42 of both eyes appears to be a viable method of reducing symptoms of pre-menstrual syndrome (PMS).

(5) A beta frequency (16 Hz) applied to the left visual fields 32/42 of both eyes and a theta (6 Hz) frequency applied to the right visual fields 34/44 of both eyes is being used to elicit a type of lucid dream in which the subject is able to be highly creative.

(6) By employing a slightly different frequency (for example 7 to 10 Hz) in the left and right visual fields of the eyes a third beat frequency can be established. This generates an abundance of sensory stimulation that reduces the internal chatter of a busy or stressed subject's mind, which speeds up the process of eliciting a meditative or hypnotic trance. The specific frequency ranges shown in Table 1 have been used in preliminary studies.

TABLE 1

| Frequency Name | Frequency Range |
| --- | --- |
| Beta 1 | 17 to 25 Hz |
| SMR | 13 to 16 Hz |
| Alpha | 8 to 12 Hz |
| Theta | 5 to 7 Hz |
| Delta | 1 to 4 Hz |

By stimulating the eyes in a left/right/left/right fashion the brain is actually stimulated at double the stimulation frequency. Consequently, the system of the present invention provides a photic stimulator capable of stimulating the left and right visual fields of each eye independently of each other.

I claim:

1. An apparatus for stimulating the central nervous system and the brain waves of a human subject having left and right eyes and left and right visual fields within each eye comprising:

light means providing pulsating light signals separately to (a) the right visual fields of the right and left eyes of the subject and (b) the left visual field of the right and left eyes of the subject; and a control module for varying frequency and intensity of the light means.

2. The apparatus of claim 1, wherein said light means comprises an eye mask having means for securing said eye mask on the subject in a position covering the left and right eyes and having left and right eye pieces located respectively proximate the left and right eyes.

3. The apparatus of claim 2, further including a reflective layer covering the left and right eye pieces of the eye mask.

4. The apparatus of claim 3, further including a translucent cover positioned over the light means, such that the light means are positioned between the reflective layer and said translucent cover.

5. The apparatus of claim 1, wherein the light means includes a light assembly for each eye consisting of a first and second light source wherein the first light source excites the left visual field and the second light source excites the right visual field of each eye.

6. The apparatus of claim 5, wherein the first and second light sources each include two pairs of lights each pair being vertically aligned within a respective visual field.

7. The apparatus of claim 6, wherein said control module includes means for simultaneous pulsating of the first light source of the light assemblies such that the left visual fields of each eye can be independently stimulated.

8. The apparatus of claim 6, wherein said control module includes means for simultaneous pulsating of the second light source of the light assemblies such that the right visual fields of each eye can be independently stimulated.

9. The apparatus of claim 6, wherein the light sources are incandescent bulbs.

10. The apparatus of claim 9, wherein the eye mask includes blocking means positioned between the first light source and the second light source of the light assembly of each eye.

11. The apparatus of claim 6, wherein the light sources are light emitting diodes.

12. The apparatus of claim 6, wherein the control module turns the light sources on and off rapidly.

13. The apparatus of claim 6, wherein the control module turns the light sources on and off sinusodally.

14. A method of stimulating the central nervous system and the brain waves of a human subject having left and right eyes and left and right visual fields within each eye comprising:

providing pulsating light signals separately to (a) the right visual fields of the right and left eyes of the subject and (b) the left visual fields of the right and left eyes of the subject; and varying frequency and intensity of the light signals.

15. The method of claim 14, wherein a first frequency of approximately 8 to 12 Hz is applied to the right visual fields of each eye and a second frequency of approximately 12 to 16 Hz is applied to the left visual fields of each eye for treating attention deficient disorder.

16. The method of claim 14, wherein a first frequency of approximately 10 to 14 Hz is applied to the right visual fields of each eye and a second frequency of approximately 16 to 20 Hz is applied to the left visual fields of each eye for treating attention deficient disorder.

17. The method of claim 14, wherein a first frequency of approximately 12 to 16 Hz is applied to the right visual fields of each eye and a second frequency of approximately 21 to 26 Hz is applied to the left visual fields of each eye for treating attention deficient disorder.

18. The method of claim 14, wherein a first frequency of approximately 10 Hz is applied to the right visual fields of each eye and a second frequency of approximately 25 Hz is applied to the left visual fields of each eye for reducing the symptoms of pre-menstrual syndrome.

19. The method of claim 14, wherein a first frequency of 16 Hz is applied to the left visual fields of each eye and a second frequency of approximately 6 Hz is applied to the right visual fields of each eye for eliciting a dream state to encourage creative thought processes.

* * * * *

UNITED STATES PATENT AND TRADEMARK OFFICE
CERTIFICATE OF CORRECTION

PATENT NO. : 5,709,645
DATED : January 20, 1998
INVENTOR(S) : David Siever

It is certified that error appears in the above-identified patent and that said Letters Patent is hereby corrected as shown below:

Column 1, line 5 should read:
"Field of the Invention"

Column 3, line 5 should read:
"visual field 44. Spacing of light sources..."

Signed and Sealed this

Tenth Day of November 1998

Attest:

BRUCE LEHMAN

Attesting Officer        Commissioner of Patents and Trademarks